US012103898B2

(12) United States Patent
Jacoby et al.

(10) Patent No.: US 12,103,898 B2
(45) Date of Patent: Oct. 1, 2024

(54) PROCESS FOR PREPARING DIENE

(71) Applicant: Firmenich SA, Satigny (CH)

(72) Inventors: Denis Jacoby, Satigny (CH); Philippe Dupau, Satigny (CH); Lucia Bonomo, Satigny (CH); Simone Chappuis, Satigny (CH); Virginie Blanchard, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 18/007,339

(22) PCT Filed: Jul. 26, 2021

(86) PCT No.: PCT/EP2021/070882
§ 371 (c)(1),
(2) Date: Jan. 30, 2023

(87) PCT Pub. No.: WO2022/023283
PCT Pub. Date: Feb. 3, 2022

(65) Prior Publication Data
US 2023/0265025 A1    Aug. 24, 2023

(30) Foreign Application Priority Data

Jul. 30, 2020 (EP) .................................... 20188772
Aug. 10, 2020 (EP) .................................... 20190199

(51) Int. Cl.
*C07C 1/20*      (2006.01)
*C07C 1/213*     (2006.01)

(52) U.S. Cl.
CPC .......... *C07C 1/213* (2013.01); *C07C 2523/44* (2013.01)

(58) Field of Classification Search
CPC ......... C07C 1/213; C07C 11/21; C07C 11/28; C07C 67/293
See application file for complete search history.

(56) References Cited

U.S. PATENT DOCUMENTS 4,652,692 A * 3/1987 Fugier .................... C07C 1/326
585/600

OTHER PUBLICATIONS

Arndt, M et al. "Gaining Absolute Control of the Regiochemistry in the Cobalt-Catalyzed 1,4-Hydrovinylation Reaction", Organic Letters, vol. 13: No. 23, (Dec. 2, 2011). pp. 6236-6239.
Arndt, M et al. "Ligand Control of the Cobalt-Catalysed 1,4-Hydrovinylation Reaction", Synthesis, vol. 44: No. 22, (Oct. 2, 2012), pp. 3534-3542.

* cited by examiner

*Primary Examiner* — Sharon Pregler
(74) *Attorney, Agent, or Firm* — Armstrong Teasdale LLP

(57) ABSTRACT

The present invention relates to the field of organic synthesis and more specifically it concerns a process for preparing compound of formula (I) catalyzed by a nickel complex. The compound of formula (II) is also part of the invention.

19 Claims, No Drawings

PROCESS FOR PREPARING DIENE

This present application is a U.S. national phase entry under 35 U.S.C. § 371 of PCT Application No. PCT/EP2021/070882, filed Jul. 26, 2021, which claims priority to European Patent Application No. 20188772.6, filed Jul. 30, 2020 and European Patent Application No. 20190199.8, filed Aug. 10, 2020. The entire contents of these applications are explicitly incorporated herein by this reference.

TECHNICAL FIELD

The present invention relates to the field of organic synthesis and more specifically it concerns a process for preparing compound of formula (I) catalyzed by a nickel complex.

The compound of formula (II) is also part of the invention.

BACKGROUND

The 1,3,5-triene or 1,3-diene-5-yne derivatives of formula (I) represent skeletons highly desirables which could be used as such or as key intermediates useful to prepare more complex compounds in different fields such as, among others, perfumery, cosmetic, pharmaceutic or agrochemistry. In particular, 1,3-Undecadien-5-yne or 1,3,5-undecatriene are valuable compounds known as perfuming ingredients imparting green note very appreciated by perfumers. However, compounds of formulas (I) are mainly obtained by Grignard reactions, which are difficult to implement in production due to high dilution in hazardous solvents and generation of significant amount of undesired wastes and, in particular, halogenated wastes. Since decades, metal-catalyzed couplings allowing to overcome the above-drawback have been largely developed, for example, in order to obtain triene building blocks as in U.S. Pat. No. 4,652,692 or eneyne building blocks. However, metal-catalysed couplings involving a triple bond need a preactivation of the triple bond by, for example, tin, silyl or carboxylic acid functional groups. Coupling on terminal triple bond has never been reported.

So, there is still a need to develop a safer and cleaner approach to access those compounds via the coupling of a terminal triple bond.

The present invention allows obtaining compound of formula (I), with high yield while limiting even avoiding the formation of the (3Z) isomers, by combining two steps, both catalysed by a nickel complex. To the best of our knowledge, both steps have never been reported in the prior art.

SUMMARY OF THE INVENTION

The invention relates to a novel process allowing the preparation of compound of formula (I) using methodologies never reported or suggested in the prior art.

So, a first object of the present invention is process for the preparation of a compound of formula (I)

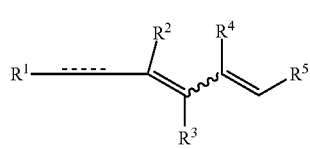

in a form of any one of its stereoisomers or a mixture thereof and wherein the dotted line is a carbon-carbon double or a carbon-carbon triple bond; $R^1$ represents a $C_{1-10}$ hydrocarbon group, optionally comprising one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups and $R^2$, $R^3$, $R^4$ and $R^5$, independently from each other, represent a hydrogen atom, a $C_{1-3}$ alkyl group or a phenyl group;

comprising the reaction of a compound of the formula (II)

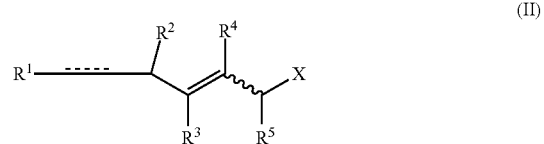

in a form of any one of its stereoisomers and wherein the dotted line, $R^1$, $R^2$, $R^3$, $R^4$ and $R^5$ have the same meaning as defined in formula (I) and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group;

with a nickel catalyst.

A second object of the present invention is a process for the preparation of a compound of formula (IV)

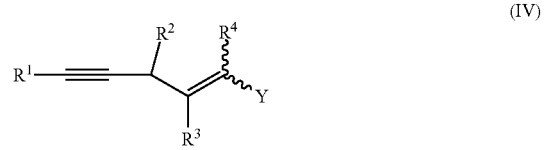

in a form of any one of its stereoisomers and wherein $R^1$ represents a $C_{1-10}$ hydrocarbon group, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$ and $R^4$, independently from each other, represent a hydrogen atom, a $C_{1-3}$ alkyl group or a phenyl group and Y is a hydrogen atom, a $C_{1-3}$ alkyl group, or a $CHR^5X$ group wherein $R^5$ is a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group;

by reacting together a compound of formula

in a form of any one of its stereoisomers and wherein $R^1$ has the same meaning as defined in formula (IV);

with a compound of formula

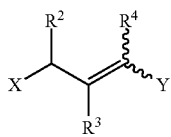
(VI)

in a form of any one of its stereoisomers and wherein X, Y, $R^2$, $R^3$ and $R^4$ independently from each other, have the same meaning as defined in formula (IV);
in the presence of a nickel catalyst.

A third object of the present invention is compound of formula

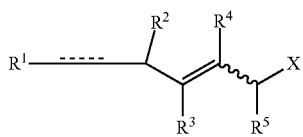
(II)

in a form of any one of its stereoisomers and wherein the dotted line is a carbon-carbon double or a carbon-carbon triple bond; $R^1$ represents a linear or branched $C_{1-10}$ alkyl group, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$, $R^4$ and $R^5$, independently from each other, represent a hydrogen atom, a $C_{1-3}$ alkyl group or a phenyl group and X represents a $OR^6$ group, a $OC(\!=\!O)R^6$ group, a $OC(\!=\!O)OR^6$ group or a $OSO_2R^6$ group, wherein $R^6$ is a hydrogen atom or a $C_{1-4}$ alkyl group or a phenyl group.

DESCRIPTION OF THE INVENTION

Surprisingly, it has now been discovered that the compound of formula (I) can be produced in an advantageous manner by means of Ni-catalyzed coupling reaction followed by a Ni-catalyzed elimination reaction. These unprecedented steps allows the generation of compounds of formula (I) wherein the double bond in position 3 are mainly E while avoiding the use of strong base and the generation of halogenated wastes.

Therefore, a first object of the present invention is a process for the preparation of a compound of formula (I)

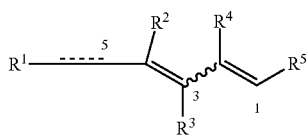
(I)

in a form of any one of its stereoisomers or a mixture thereof and wherein the dotted line is a carbon-carbon double or a carbon-carbon triple bond and $R^1$ represents a $C_{1-10}$ hydrocarbon group, optionally comprising one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups and $R^2$, $R^3$, $R^4$ and $R^5$, independently from each other, represent a hydrogen atom, a $C_{1-3}$ alkyl group or a phenyl group;
comprising the reaction of a compound of the formula (II)

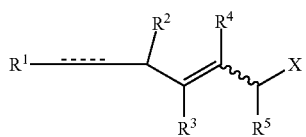
(II)

in a form of any one of its stereoisomers and wherein the dotted line, $R^1$, $R^2$, $R^3$, $R^4$ and $R^5$ have the same meaning as defined in formula (I) and X represents a $OR^6$ group, a $OC(\!=\!O)R^6$ group, a $OC(\!=\!O)OR^6$ group or a $OSO_2R^6$ group, wherein $R^6$ is a hydrogen atom or a $C_{1-4}$ alkyl group or a phenyl group;
with a nickel catalyst.

For the sake of clarity, by the expression "any one of its stereoisomers or a mixture thereof", or the similar, it is meant the normal meaning understood by a person skilled in the art, i.e. that the compounds cited in the invention can be a pure enantiomer or a mixture of enantiomers. In other words, the compounds cited in the invention may possess at least one stereocenter which can have two different stereochemistries (e.g. R or S), e.g. the $R^1$ group may comprise at least one stereocenter. Said compounds may even be in the form of a pure enantiomer or in the form of a mixture of enantiomers. The compounds cited in the invention may even be in the form of a pure diastereoisomer or in the form of a mixture of diastereoisomers when said compounds possess more than one stereocenter. Said compounds can be in a racemic form or scalemic form. Therefore, said compounds can be one stereoisomer or in the form of a composition of matter comprising, or consisting of, various stereoisomers.

The wavy line indicates that the double bond may be in the form of its E or Z isomer or of a mixture thereof; e.g. the invention comprises compositions of matter consisting of one or more compounds of formula (I), having the same chemical structure but differing by the configuration of the double bond.

According to any one of the above embodiments of the invention, the compound of formula (I) can be in the form of its E or Z isomer or of a mixture thereof, e.g. the invention comprises compositions of matter consisting of one or more compounds of formula (I), having the same chemical structure but differing by the configuration of the doubles bond. According to a particular embodiment of the invention, compound (I) can be in the form of a mixture consisting of isomers 3E and 3Z and wherein said isomer 3E represent at least 50% of the total mixture, or even at least 75%, or even at least 90% (i.e a mixture E/Z comprised between 90/10 and 100/0). According to another particular embodiment of the invention, compound (I) can be in the form of a mixture consisting of isomers (3E,5Z) and (3Z,5Z) and wherein said isomer (3E,5Z) represent at least 50% of the total mixture, or even at least 75, or even at least 90% (i.e a mixture E/Z comprised between 90/10 and 100/0).

For the sake of clarity, by the expression "wherein the dotted line is a carbon-carbon double or a carbon-carbon triple bond", or the similar, it is meant the normal meaning understood by a person skilled in the art, i.e. that the whole bonding (solid and dotted line) between the carbon atoms connected by said dotted line is a carbon-carbon double bond or is a carbon-carbon triple bond.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

The term "optionally" is understood that a group can or cannot comprise a certain functional group. The term "one or more" is understood as comprising 1 to 7, preferably 1 to 5 and more preferably 1 to 3 functional groups.

According to any embodiment of the invention, $R^1$ may be a $C_{1-10}$ hydrocarbon group, optionally comprising one or more hydroxy, $C_{1-5}$ alkoxy, $C_{2-5}$ alkenyloxy, $C_{3-6}$ heterocycloalkyl, $C_{6-10}$ aryloxy and/or $C_{1-4}$ carboxylic ester groups. Particularly, $R^1$ may be $C_{1-10}$ alkyl group or a linear $C_{2-10}$ alkenyl group, optionally comprising one hydroxy or $C_{1-4}$ carboxylic ester group. Particularly, $R^1$ may be a linear $C_{1-10}$ alkyl group, a linear $C_{2-10}$ alkenyl group, a branched $C_{3-10}$ alkyl or alkenyl group, a cyclic $C_{5-10}$ alkyl or alkenyl group, or a $C_{6-10}$ aryl group, optionally comprising one hydroxy or $C_{1-4}$ carboxylic ester group. Particularly, $R^1$ may be a linear $C_{1-10}$ alkyl group, a linear $C_{2-10}$ alkenyl group, a branched $C_{3-10}$ alkyl or alkenyl group, or a $C_{6-10}$ aryl group, optionally comprising one hydroxy or $C_{1-4}$ carboxylic ester group. Particularly, $R^1$ may be a linear $C_{1-10}$ alkyl group, a branched $C_{3-10}$ alkyl group, or a $C_{6-10}$ aryl group. Particularly, $R^1$ may be a linear $C_{1-10}$ alkyl group, a branched $C_{3-10}$ alkyl group, or a phenyl group. Particularly, $R^1$ may be a linear $C_{4-8}$ alkyl group. Even more particularly, $R^1$ may be a pentyl group.

According to any embodiment of the invention, $R^2$, $R^3$, $R^4$ and $R^5$, independently from each other, may be a hydrogen atom or a $C_{1-3}$ alkyl group. Particularly. $R^2$, $R^3$, $R^4$ and $R^5$, independently from each other, may be a hydrogen atom or a methyl or ethyl group. Particularly, $R^2$, $R^3$, $R^4$ and $R^5$ independently from each other, may be a hydrogen atom or a methyl group. Particularly, two groups among $R^2$, $R^3$, $R^4$ and $R^5$, independently from each other, may be a hydrogen atom or a methyl group and the others are hydrogen atom. Particularly, one group among $R^2$, $R^3$, $R^4$ and $R^5$, independently from each other, may be a hydrogen atom or a methyl group and the others are hydrogen atom. Even more particularly, $R^2$, $R^3$, $R^4$ and $R^5$ may be a hydrogen atom.

According to any embodiment of the invention, $R^6$ may be a $C_{1-3}$ alkyl group. Particularly, $R^6$ may be a methyl or an ethyl group. Even mora particularly, $R^6$ may be a methyl group.

According to any embodiment of the invention, X may represent a $OC(=O)R^6$ group wherein $R^6$ is a hydrogen atom or a $C_{1-4}$ alkyl group or a phenyl group. Particularly, X represents a $OC(=O)R^6$ group wherein $R^6$ is a $C_{1-3}$ alkyl group. Even more particularly, X represents a acetate group.

The terms "alkyl", "alkoxy" and "alkenyl" are understood as comprising branched and linear alkyl and alkenyl groups. The terms "alkenyl" and "alkenyloxy" are understood as comprising 1, 2 or 3 olefinic double bonds, preferably 1 or 2 olefinic double bonds. The terms "heterocycloalkyl is understood as comprising a monocyclic or fused, spiro and/or bridged bicyclic or tricyclic heterocycloalkyl group, preferably monocyclic heterocycloalkyl groups. The terms "heterocycloalkyl is understood as a cycloalkyl comprising one or more heteroatoms, in particular comprising one or two oxygen atoms.

The term "aryl" or "aryloxy" is understood as comprising any group comprising at least one aromatic group such as phenyl, indenyl, indanyl, benzodioxolyl, dihydrobenzodioxinyl, tetrahydronaphthalenyl or naphthalenyl group.

According to a particular embodiment of the invention, the dotted line is a triple bond. In other words, the compound of formula (I) is a compound of formula

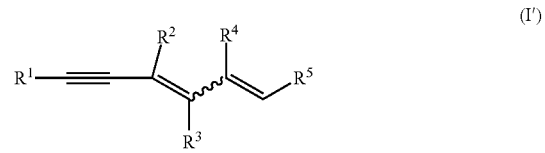

(I')

in a form of any one of its stereoisomers or a mixture thereof and wherein $R_1$, $R^2$, $R^3$, $R^4$ and $R^5$ have the same meaning as defined above. And, the compound of formula (II) is of formula

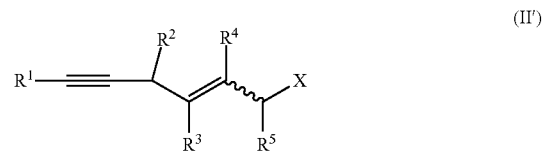

(II')

in a form of any one of its stereoisomers and wherein $R^1$, $R^2$, $R^3$, $R^4$, $R^5$ and X have the same meaning as defined above.

According to a particular embodiment of the invention, the dotted line is a double bond. In other words, the compound of formula (I) is of formula

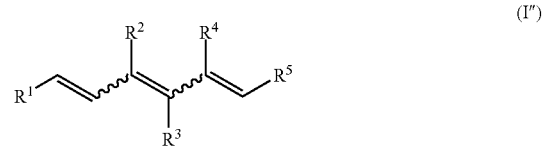

(I")

in a form of any one of its stereoisomers or a mixture thereof and wherein $R^1$, $R^2$, $R^3$, $R^4$ and $R^5$ have the same meaning as defined above. And, the compound of formula (II) is of formula

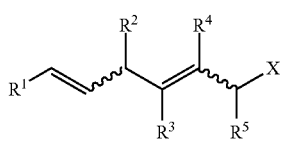
(II'')

in a form of any one of its stereoisomers and wherein $R^1$, $R^2$, $R^3$, $R^4$, $R^5$ and X have the same meaning as defined above. The compound of formula (II'') is obtained by the reduction of the compound of formula (II'). According to any embodiment of the invention, the reduction is an hydrogenation. Particularly, the hydrogenation may be carried out in a presence of heterogeneous catalyst such as palladium ($Pd^0$) in elemental metallic form. Particularly, said palladium may be supported on a carrying material. For the sake of clarity, by carrying material it is intended a material wherein it is possible to deposit such metal and which is inert toward the hydrogen source and the substrate. The supported palladium ($Pd^0$) are known compounds and are commercially available. A person skilled in the art is able to select the way that it was deposit on the support, as the proportion of metal on support material, as the form (powder, granules, pellets, extrudates, mousses . . . ) and as the surface area of the support. Particularly, the hydrogenation may be carried out with heterogeneous catalyst favorizing the formation of the Z double bond. Particularly, the heterogeneous catalyst is a Lindlar catalyst. The hydrogenation may be carried out under conditions known by the person skilled in the art who will be able to set up the best conditions in order to convert compound of formula (II') into compound of formula (II'').

Non-limiting examples of suitable compounds of formula (I) may include 1,3-undecadien-5-yne, (3E)-1,3-undecadien-5-yne, 1,3,5-undecatriene, (3E,5Z)-1,3,5-undecatriene, (hexa-3,5-dien-1-yn-1-yl)benzene, ((1Z,3E)-hexa-1,3,5-trien-1-yl)benzene, ethyl nona-6,8-dien-4-ynoate, ethyl (4Z,6E)-nona-4,6,8-trienoate, (2E)-3-methylnona-2,6,8-trien-4-yn-1-ol, (2E,4Z,6E)-3-methylnona-2,4,6,8-tetraen-1-ol, 2-methylocta-5,7-dien-3-yn-2-ol, (3Z,5E)-2-methylocta-3,5,7-trien-2-ol, octa-5,7-dien-3-yn-1-ol and (3Z,5E)-octa-3,5,7-trien-1-ol.

Non-limiting examples of suitable compounds of formula (II) may include undec-2-en-5-yn-1-yl acetate, (E)-undec-2-en-5-yn-1-yl acetate, undeca-2,5-dien-1-yl acetate, (2E,5Z)-undeca-2,5-dien-1-yl acetate, (E)-6-phenylhex-2-en-5-yn-1-yl acetate, (2E,5Z)-6-phenylhexa-2,5-dien-1-yl acetate, ethyl (E)-9-acetoxynon-7-en-4-ynoate, ethyl (4Z,7E)-9-acetoxynona-4,7-dienoate, (2E,7E)-9-hydroxy-7-methylnona-2,7-dien-5-yn-1-yl acetate, (2E,5Z,7E)-9-hydroxy-7-methylnona-2,5,7-trien-1-yl acetate, (E)-7-hydroxy-7-methyloct-2-en-5-yn-1-yl acetate, (2E,5Z)-7-hydroxy-7-methylocta-2,5-dien-1-yl acetate, (E)-8-hydroxyoct-2-en-5-yn-1-yl acetate and (2E,5Z)-8-hydroxyocta-2,5-dien-1-yl acetate.

According to any embodiments of the invention, the nickel catalyst is of formula

[Ni(P)$_4$]     (III) or

[Ni(PP)$_2$]     (III') . . . or

[Ni(P)$_2$ML]     (III'') or

[Ni(PP)ML]     (III''')

wherein each P represents, independently from each other, a $C_3$-$C_{30}$ monodentate ligand wherein the coordinating groups are one phosphorus atom and each PP represents, independently from each other, a $C_5$-$C_{50}$ bidentate ligand wherein the coordinating groups are two phosphorus atoms; and M and L, independently from each other, are an anionic or neutral ligand, provided that when M is a neutral ligand, L is a neutral ligand and when M is an anionic ligand, L is an anionic ligand.

Non-limiting examples of suitable anionic ligand may include halogen atom such as Cl, Br or I. Non-limiting examples of suitable neutral ligand may include olefin containing compound such as acrylonitrile or ML may be a diene such as cycloocta-1,5-diene.

According to any embodiments of the invention, the nickel catalyst is of formula

[Ni(P)$_4$]     (III) or

[Ni(PP)$_2$]     (III')

wherein each P represents, independently from each other, a $C_3$-$C_{30}$ monodentate ligand wherein the coordinating groups are one phosphorus atom and each PP represents, independently from each other, a $C_5$-$C_{50}$ bidentate ligand wherein the coordinating groups are two phosphorous atoms.

According to any embodiments of the invention, the phosphorus atom may be in a form of a phosphine or a phosphite group.

According to any embodiments of the invention, the ligand (PP) may be selected from the group consisting of 1,2-bis(diphenylphosphino)ethane and 1,4-bis(diphenylphosphino)butane.

According to any one of the invention's embodiments, the ligand P may be a $C_3$-$C_{30}$ monophosphine monodentate ligand or monophosphite monodentate ligand. Particularly, the ligand P may represent a mono-phosphite of formula P(OR$^7$)$_3$ or a mono-phosphine of formula PR$^7_3$, wherein R$^7$ is a $C_1$-$C_{10}$ group, such as linear, branched or cyclic alkyl group or a phenyl, diphenyl, naphthyl or di-naphthyl group, each optionally substituted. Particularly, R$^7$ may represent a $C_{1-8}$ linear alkyl group, a $C_{3-8}$ branched alkyl group or a phenyl group optionally substituted. Particularly, R$^7$ may represent a $C_{1-6}$ linear alkyl group, a $C_{3-6}$ branched alkyl group or a phenyl group optionally substituted. More particularly, R$^7$ may represent a $C_{1-3}$ linear alkyl group or a $C_3$ branched alkyl group. Possible optional substituents are one, two, three or four groups selected amongst i) halogens (in particular when said substituents are on aromatic moieties), ii) $C_{1-6}$ alkoxy, alkyl, alkenyl, or iii) a benzyl group or a fused or non-fused phenyl group, said group being optionally substituted by one, two or three halogen, $C_{1-8}$ alkyl, alkoxy, amino, nitro, ester, sulfonate or halo- or perhalohydrocarbon groups.

According to any a particular invention's embodiments, the ligand P may be a mono-phosphite of formula P(OR$^7$)$_3$ wherein R$^7$ has the same meaning as define above.

According to any embodiments of the invention, the ligand P may be selected from the group consisting of triisopropyl phosphite, triphenyl phosphine, trioctyl phosphine, tricyclohexyl phosphine, trimethyl phosphite, triethyl phosphite and triphenyl phosphite.

According to any embodiments of the invention, the nickel catalyst is of formula (III) or (III'). Particularly, the nickel catalyst is of formula (III).

The nickel catalyst can be added into the reaction medium of the invention's process to form compound of formula (I) in a large range of concentrations. As non-limiting examples, one can cite, as nickel catalyst concentration values those ranging from 0.1 mol % to 7.5 mol %, relative to the total amount of substrate. Particularly, the nickel catalyst concentration may be comprised between 3 mol % to 6 mol %. It goes without saying that the process works also with more catalyst. However the optimum concentration of nickel catalyst will depend, as the person skilled in the art knows, on the nature of the latter, on the nature of the substrate, on the temperature and on the desired time of reaction.

The nickel catalyst is commercially available compound or can be prepared by several methods, such as the one reported in *Inorganic Chemistry* 1964, 3,1062. the nickel catalyst of formula (III) or (III') or (III") or (III''') is formed in situ by the reaction between a nickel(II) complex and a phosphine or a phosphite, being the P or PP ligand as defined above in the presence of a base such as an amine. The nickel(II) complex is hydrated. The nickel(II) complex may be selected from the group consisting of $NiCl_2(H_2O)_x$, $NiBr_2(H_2O)_x$, $Ni(OAc)_2(H_2O)_x$, $NiSO_4(H_2O)_x$ and $NiI_2(H_2O)_x$ wherein x is an integer between 1 to 7.

According to any embodiments of the invention, the invention's process to form compound of formula (I) may be performed in absence of any additives such as base or acid.

According to any one of the invention's embodiments, the invention's process to form compound of formula (I) is carried out at a temperature comprised between 0° C. and 150° C. In particular, the temperature is in the range between 30° C. and 70° C. Of course, a person skilled in the art is also able to select the preferred temperature as a function of the melting and boiling point of the starting and final products as well as the desired time of reaction or conversion.

The invention's process to form compound of formula (I) can be carried out in the presence or absence of a solvent. When a solvent is required or used for practical reasons, then any solvent current in such reaction type can be used for the purposes of the invention. Non-limiting examples include $C_{6-12}$ aromatic solvents such as xylene, toluene, 1,3-diisopropylbenzene, cumene or pseudocumene, or mixtures thereof, hydrocarbon solvents such as cyclohexane, heptane or mixtures thereof, nitrile solvent such as acetonitrile, esteral solvents such as ethyl acetate or ethereal solvents such as tetrahydrofuran, diethyether, methyl tetrahydrofuran or mixtures thereof. The choice of the solvent is function of the nature of the substrate and/or catalyst and the person skilled in the art is well able to select the solvent most suitable in each case to optimize the reaction.

The invention's process to form compound of formula (I) is carried out under batch or continuous conditions.

The invention's process to form compound of formula (I) may be performed under atmospheric pressure.

Surprisingly, the invention's process to form compound of formula (I) allows forming compound of formula (I) with the double bond in position 3 mainly with a E configuration.

The compound of formula (IV), such as compound of formula (II'), is obtained by a coupling between an alkyne of formula (V) and a compound of formula (VI). Metal-catalysed cross coupling reaction have been widely reported in the prior arts and, in particular, palladium-catalysed cross coupling reaction. However, all conditions reported in the prior art failed to provide compound of formula (IV) by starting from alkyne of formula (V) and a compound of formula (VI). So, a novel cross-coupling reaction, never mentioned or suggested in the prior arts, has been developed using a cheaper catalyst than palladium.

So, another object of the present invention is a process for the preparation of a compound of formula (IV)

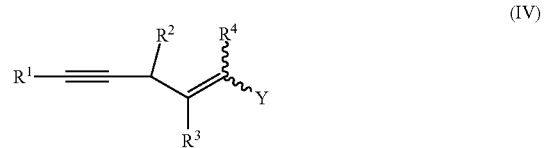

(IV)

in a form of any one of its stereoisomers and wherein $R^1$ represents a $C_{1-10}$ hydrocarbon group, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$ and $R^4$, independently from each other, represent a hydrogen atom, a $C_{1-3}$ alkyl group or a phenyl group and Y is a hydrogen atom, a $C_{1-3}$ alkyl group, or a $CHR^5X$ group wherein $R^5$ is a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group;

by reacting together a compound of formula

(V)

in a form of any one of its stereoisomers and wherein R has the same meaning as defined in formula (IV);

with a compound of formula

(VI)

in a form of any one of its stereoisomers and wherein X, Y, $R^2$, $R^3$, $R^4$ and $R^5$, independently from each other, have the same meaning as defined in formula (IV);

in the presence of a nickel catalyst.

Surprisingly, the invention's process to form compound of formula (IV) allows forming compound of formula (IV) while limiting the formation of the branched compound of formula (IV')

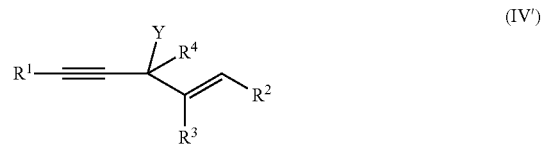

(IV')

in a form of any one of its stereoisomers and wherein $R^1$, Y, $R^2$, $R^3$, $R^4$ and $R^5$ have the same meaning as defined above. In particular, at most 50%, even at most 40%, even at most 30%, even at most 25%, even at most 20% of compound of formula (IV'), even at most 15% of compound of formula (IV') are formed.

According to any embodiments of the invention, Y may be a hydrogen atom or a $CHR^5X$ group wherein $R^5$ is a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group. Particularly, Y may be a $CHR^5X$ group wherein $R^5$ is a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group According to any embodiment of the invention, the compound of formula (IV) is of formula (II')

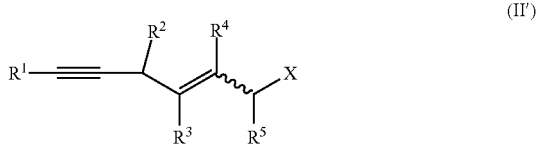

(II')

in a form of any one of its stereoisomers and wherein $R^1$ represents a $C_{1-10}$ hydrocarbon group, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$, $R^4$ and $R^5$, independently from each other, represent a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group.

According to any embodiment of the invention, the compound of formula (VI) is of formula (VII)

(VII)

in a form of any one of its stereoisomers and wherein $R^2$, $R^3$, $R^4$, $R^5$ and each X, independently from each other, have the same meaning as defined in formula (II').

According to any embodiment of the invention, the nickel catalyst is of formula (III), (III'), (III") or (III''') and have the same meaning as defined above; i.e. as defined for the invention's process to prepare compound of formula (I). Particularly, the nickel catalyst may be of formula (III) or (III") wherein the P ligand may be a monophosphite monodentate ligand.

The nickel catalyst used in both steps may be different or similar. Particularly, the nickel catalyst used in both steps is $Ni(P(Oi-Pr)_3)_4$. Both steps may be carried out in one pot.

The nickel catalyst can be added into the reaction medium of the invention's process to form compound of formula (IV) in a large range of concentrations. As non-limiting examples, one can cite, as nickel catalyst concentration values those ranging from 0.1 mol % to 7.5 mol %, relative to the total amount of substrate. Particularly, the nickel catalyst concentration may be comprised between 3 mol % to 6 mol %. It goes without saying that the process works also with more catalyst. However the optimum concentration of nickel catalyst will depend, as the person skilled in the art knows, on the nature of the latter, on the nature of the substrate, on the temperature and on the desired time of reaction.

Non-limiting examples of suitable compounds of formula (V) may include 1-propyne, 1-butyne, 1-heptyne, 1-pentyne, 1-hexyne, 1-octyne, 1-nonyne, 1-decyne, phenylacetylene, ethyl 4-pentynoate, (E)-3-methylpent-2-en-4-yn-1-ol, 2-Methyl-3-butyn-2-ol, 7-methyl-3-methyleneoct-6-en-1-yne, 1-ethynyl-3,3-dimethylcyclohexan-1-ol, 1-ethynyl-5,5-dimethylcyclohex-1-ene, 1-ethynyl-3,3-dimethylcyclohex-1-ene and 3-butyn-1-ol.

Non-limiting examples of suitable compounds of formula (VI) may include but-2-ene-1,4-diyl diacetate, but-2-ene-1,4-diyl dipropionate, but-2-ene-1,4-diyl dibenzoate, but-2-ene-1,4-diyl dipivalate, allyl acetate, 3-buten-2-yl acetate, crotyl acetate, prenyl acetate and cinnamyl acetate.

Non-limiting examples of suitable compounds of formula (IV) may include undec-2-en-5-yn-1-yl acetate, (E)-undec-2-en-5-yn-1-yl acetate, (E)-6-phenylhex-2-en-5-yn-1-yl acetate, ethyl (E)-9-acetoxynon-7-en-4-ynoate, (2E,7E)-9-hydroxy-7-methylnona-2,7-dien-5-yn-1-yl acetate, (E)-8-hydroxyoct-2-en-5-yn-1-yl acetate, dec-1-en-4-yne, (E)-7-hydroxy-7-methyloct-2-en-5-yn-1-yl acetate, (E)-undec-2-en-5-yne, 10-methyl-6-methyleneundeca-1,9-dien-4-yne, 3,3-dimethyl-1-(pent-4-en-1-yn-1-yl)cyclohexan-1-ol, 5,5-dimethyl-1-(pent-4-en-1-yn-1-yl)cyclohex-1-ene, 3,3-dimethyl-1-(pent-4-en-1-yn-1-yl)cyclohex-1-ene, dec-1-en-4-yne and ethyl oct-7-en-4-ynoate.

According to any embodiments of the invention, the invention's process to form compound of formula (IV) may be performed in absence of any additives such as base or acids.

According to any one of the invention's embodiments, the invention's process to form compound of formula (IV) is carried out at a temperature comprised between 0° C. and 150° C. In particular, the temperature is in the range between 15° C. and 30° C. Of course, a person skilled in the art is also able to select the preferred temperature as a function of the melting and boiling point of the starting and final products as well as the desired time of reaction or conversion.

The invention's process to form compound of formula (IV) can be carried out in the presence or absence of a solvent. When a solvent is required or used for practical reasons, then any solvent current in such reaction type can be used for the purposes of the invention. Non-limiting examples include $C_{6-12}$ aromatic solvents such as xylene, toluene, 1,3-diisopropylbenzene, cumene or pseudocumene, or mixtures thereof, hydrocarbon solvents such as cyclohexane, heptane or mixtures thereof, nitrile solvent such as acetonitrile, esteral solvent such as isopropyl acetate. The choice of the solvent is function of the nature of the substrate and/or catalyst and the person skilled in the art is well able to select the solvent most suitable in each case to optimize the reaction.

The invention's process to form compound of formula (IV) is carried out under batch or continuous conditions.

The invention's process to form compound of formula (IV) may be performed under atmospheric pressure.

The compound of formula (II) is novel compound and present a number of advantages as explained above and shown in the Examples.

Therefore, another object of the present invention is a compound of formula

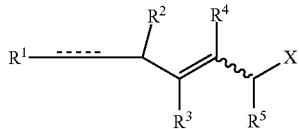

(II)

in a form of any one of its stereoisomers and wherein the dotted line is a carbon-carbon double or a triple bond; $R^1$ represents a linear or branched $C_{1-10}$ alkyl, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$, $R^4$ and $R^5$, independently from each other, represent a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group.

According to a particular embodiment, the compound of formula (II) is of formula

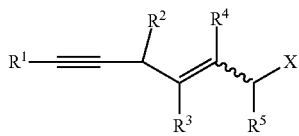

(II')

in a form of any one of its stereoisomers and wherein $R^1$ represents a linear or branched $C_{1-10}$ alkyl group, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$, $R^4$ and $R^5$ independently from each other, represent a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group.

Typical manners to execute the invention's process are reported herein below in the examples.

EXAMPLES

The invention will now be described in further detail by way of the following examples, wherein the abbreviations have the usual meaning in the art, the temperatures are indicated in degrees centigrade (° C.). The preparation of precatalysts and ligands solutions were carried out under an inert atmosphere (Argon) using standard Schlenk techniques. The solvents were dried by conventional procedures and distilled under an argon atmosphere. NMR spectra were recorded at 20° C. on Bruker AV 300, AV 400, or AV 500 MHz spectrometers. Chemical shifts are reported in ppm relative to solvent signals (chloroform, $d_H$=7.26 ppm, $d_C$=77.0 ppm). The signal assignment was ensured by recording $^1H,^1H$—COSY, —NOESY, $^{13}C,^1H$-HSQC and -HMBC experiments. Gas chromatography was performed on an Agilent 7890 A Series equipped with a HP5 column (30 m×0.25 mm ID, 0.25 μm film) and tetradecane was used as internal standard.

Example 1

Preparation of (E)-undec-2-en-5-yn-1-yl acetate 27 g (0.25eq) of triethylamine was introduced into a stirred suspension of 13 g (0.05 eq) of nickel dichloride hexahydrate and 28.5 g (0.125 eq) of triisopropylphosphite in 150 ml of isopropylacetate. 188 g (1 eq) of 1,4-Diacetoxy (Z)-But-2en then 105 g (1eq) of 1-heptyne were introduced and the mixture was stirred at 20° C. overnight. Then the reaction was treated by aqueous Na₂EDTA followed by diluted potassium carbonate. The resulting product was concentrated under vacuum then 230 g are flash distilled then fractionated on packed 3 m Sulzer lab still equipment. A first fraction (50° C./5 mbar) consisting of unreacted 1-Heptyne (24 g, 22.8%) was recovered, followed by a second fraction (55-85° C./3 mbar) consisting of a mixture of unreacted 1,4-diacetoxy but-2-ene and 2-vinylnon-3-yn-1-yl acetate (81 g) and a third fraction (102-110° C./3 mbar) consisting of (E)-undec-2-en-5-yn-1-yl acetate (109 g, 98% purity, 48% yield).

(E)-Undec-2-En-5-Yn-1-Yl Acetate $^1H$ NMR (CD₂Cl₂, 500 MHz) δ 0.9 (t, J=7.0 Hz, 3H, CH₃); 1.34 (series of m, 4H, CH₂); 1.49 (m, 2H, CH₂); 2.03 (s, 3H, CH₃); 2.17 (m, 2H, CH₂); 2.9 (m broad, 2H, CH₂); 4.5 (d broad, J=6.2 Hz, 2H, CH₂); 5.75 (m, 1H, CH); 5.85 (m, 1H, CH).
$^{13}C$ NMR (CD₂Cl₂, 125 MHz), δ 14.2 (CH₃), 19.0 (CH₂), 21.1 (CH₃), 22.2 (CH₂), 22.6 (CH₂), 29.2 (CH₂), 31.5 (CH₂), 64.8 (CH₂), 76.4 (C), 83.4 (C), 125.6 (=CH), 130.7 (=CH), 170.9 (CO).

Example 2

Preparation of (3E/Z)-1,3-Undecadien-5-yne

A suspension of 5.7 g of Nickel dichloride hexahydrate was stirred at 25° C. in 200 g of acetonitrile in the presence of 15 g of triisopropylphosphite. After 1 h of stirring, 36 g of triethylamine was loaded, followed by 100 g of (E)-undec-2-en-5-yn-1-yl acetate. Then, the mixture was heated to 50° C. over 5 h. On completion of the reaction, the mixture was cooled to 35° C., taken by 200 g Cyclohexane and washed twice by aqueous Na₂EDTA. Finally, the mixture was neutralized by diluted potassium bicarbonate and evaporated to dryness. The resulting oil (90 g) was flash distilled (50° C./1 mbar) affording 58 g of 1,3-Undecadien-5-yne (E/Z ratio 73:27) in 97% purity and 79% yield.

(3E)-1,3-Undecadien-5-yne $^1H$ NMR (CDCl₃, 400 MHz) δ 0.88 (t, J=7.1 Hz, 3H, CH₃); 1.36 (series of m, 4H, CH₂); 1.53 (m, 2H, CH₂); 2.3 (m, 2H, CH₂); 5.12 (d broad, J=9.9 Hz, 1H, CH₂); 5.24 (d broad, J=16.2 Hz, 1H, CH₂); 5.63 (d, J=15.1 Hz, 1H, CH); 6.35 (dd, J₁=15.1 Hz, J₂=16.2 Hz, J₃=6.5 Hz, 1H, CH); 6.49 (dd, J₁=15.1 Hz, J₂=16.2 Hz, 1H, CH).
$^{13}C$-NMR (CDCl₃, 90 MHz) δ 13.9 (CH₃), 19.6 (CH₂), 22.2 (CH₂), 28.5 (CH₂), 31.1 (CH₂), 79.6 (C), 93.6 (C), 112.8 (=CH), 118.4 (=CH₂), 136.4 (=CH), 140.9 (=CH).

Example 3

Preparation of (2E,5Z)-undeca-2,5-dien-1-yl (E)-undec-2-en-5-yn-1-yl acetate, Lindlar catalyst (0.11 wt. %, 0.011 mol. % Pd) and 3,6-dithia-1,8-octanediol (Lindlar catalyst poison, CAS number: 5244-34-8) (0.0014 wt. %, 0.0016 mol. % i.e. about 15 mol. % respect to Pd) were loaded altogether in a 100 mL or 1 L autoclave equipped with a mechanical sitting device, pressure and internal temperature sensors and a heating/cooling system for internal temperature regulation. Sealed autoclave was then purged under stirring with nitrogen (3 times 5 bars) before being stirred at 25° C. under 1 bar nitrogen pressure for 30 minutes. After this period, autoclave was purged under stirring with hydrogen (3 times 1 bar) before being pressurized to 1 bar hydrogen pressure via an hydrogen tank equipped with a way out pressure regulator and also and internal pressure sensor to follow and determine hydrogen consumption. Reaction mixture was then stirred (1000 rnd./min) at 50° C. under 3 bars hydrogen pressure, pressure being maintained to this value during the whole reaction. Upon alkyne hydrogenation completion (2 to 3 hours) also determined by GC analysis on a short polar column (DB-Wax 10 m×0.1 mm×0.1 mm), autoclave was cooled down to room temperature, stirring was stopped and autoclave was depressurized and purged with nitrogen (3 times 5 bars). Reaction mixture was passed through some filtration equipment to remove Lindlar catalyst. Desired (2E,5Z)-undeca-2,5-dien-1-yl acetate was obtained with complete conversion, 99/1 (2E,5Z)/(2E,5E) ratio, more than 99.5% GC chemoselectivity and no residues formed (determined by sample bulb to bulb distillation) without any further purification.

(2E,5Z)-Undeca-2,5-Dien-1-Yl Acetate $^1$H NMR (400 MHz, $CD_2Cl_2$): d (ppm) 0.88 (t, J=6.9 Hz, 3H, $CH_3$), 1.20-1.40 (m, 6H, 3 $CH_2$), 1.98-2.08 (m, 5H, $CH_2+CH_3$), 2.80 (t, J=6.8 Hz, 2H, $CH_2$), 4.48 (dd, $J_1$=6.4, $J_2$=1.0 Hz, 2H, $CH_2$), 5.30-5.40 (m, 1H, =CH), 5.42-5.52 (m, 1H, =CH), 5.53-5.63 (m, 1H, =CH), 5.70-5.80 (m, 1H, =CH).
$^{13}$C NMR (100 MHz, $CD_2Cl_2$): d (ppm) 14.2 ($CH_3$), 21.1 ($CH_3$), 23.0 ($CH_2$), 27.5 ($CH_2$), 29.7 ($CH_2$), 30.4 ($CH_2$), 31.9 ($CH_2$), 65.3 ($CH_2$), 124.7 (=CH), 126.5 (=CH), 131.9 (=CH), 134.6 (=CH), 170.9 (CO).

Example 4

Preparation of (3E,5Z)-1,3,5-undecatriene

A suspension of 5.7 g of nickel dichloride hexahydrate was stirred at 25° C. in 200 g of acetonitrile in the presence of 15 g of triisopropylphosphite. After 1 h of stirring, 36 g of triethylamine was loaded, followed by 100 g of (2E,5Z)-undeca-2,5-dien-1-yl acetate (Ib). Then, the mixture was heated to 50° C. over 5 h. On completion of the reaction, the mixture was cooled to 35° C., taken by 200 g Cyclohexane and washed twice by aqueous $Na_2EDTA$. Finally, the mixture was neutralized by diluted potassium bicarbonate and evaporated to dryness. The resulting oil (92 g) was flash distilled (50° C./1 mbar) affording 63 g of (3E,5Z)-1,3,5-undecatriene (3E/3Z ratio 98:2) in 95% purity and 85% yield.

(3E,5Z)-1,3,5-undecatriene $^1$H NMR ($CDCl_3$, 400 MHz) δ 0.89 (t, J=7.1 Hz, 3H, $CH_3$), 1.31 (series of m, 4H, $CH_2$), 1.38 (m, 2H, $CH_2$), 2.2 (m, 2H, $CH_2$); 5.12 (d broad, J=10.6 Hz, 1H, $CH_2$), 5.24 (d broad, J=17.0 Hz, 1H, $CH_2$), 5.5 (m, 1H, CH), 6.0 (t broad, J=15.1 Hz, 1H, CH), 6.2 (dd, $J_1$=15.1 Hz, $J_2$=10.6 Hz, 1H, CH), 6.4 (m, 2H, CH).
$^{13}$C NMR ($CDCl_3$, 100 MHz) δ 14.0 ($CH_3$), 22.7 ($CH_2$), 27.9 ($CH_2$), 29.5 ($CH_2$), 31.6 ($CH_2$), 116.7 (=$CH_2$), 128.4 (CH), 128.8 (CH), 133.0 (CH), 133.6 (CH), 137.4 (CH).

Example 5

Preparation of (E)-6-Phenylhex-2-en-5-vn-1-yl acetate 0.66 g (0.25eq) of triethylamine was introduced into a stirred suspension of 0.31 g (0.05 eq) of nickel dichloride hexahydrate and 0.68 g (0.125 eq) of triisopropylphosphite in 3.6 ml of isopropylacetate. 4.48 g (1eq) of 1,4-Diacetoxy (Z)-But-2-ene then 2.66 g (1eq) of phenylacetylene were introduced and the mixture was stirred at 20° C. overnight. Then the reaction was treated by aqueous $Na_2EDTA$ followed by diluted potassium carbonate. The reaction mixture containing 31% GC of unreacted phenylacetylene, 46% GC of (E)-6-phenylhex-2-en-5-yn-1-yl acetate and 15% GC of 2-(phenylethynyl)but-3-en-1-yl acetate (75/25 linear/branched ratio) was purified by chromatography on silica gel (30/50 petroleum ether/Et2O 10/0 to 9/1) for pure products isolation.

(E)-6-phenylhex-2-en-5-yn-1-yl acetate (Major Product)

$^1$H NMR ($CDCl_3$, 500 MHz) δ 2.07 (s, 3H, $CH_3$), 3.21 (broad dq, J=5.2 and 1.4 Hz, 2H, $CH_2$), 4.59 (broad dq, J=6.2 and 1.1 Hz, 2H, $CH_2$), 5.84 (dtt, J=15.2, 5.2 and 1.1 Hz, 1H, CH alkene), 5.94 (dtt, J=15.2, 6.2 and 1.4 Hz, 1H, CH alkene), 7.27-7.32 (m, 3H, 3 CH Ar), 7.39-7.45 (m, 2H, 2 CH Ar).
$^{13}$C NMR ($CDCl_3$, 125 MHz), δ 21.0 ($CH_3$), 22.4 ($CH_2$), 64.5 ($CH_2$), 83.0 (C alkyne), 86.1 (C alkyne), 123.5 (C Ar), 125.8 (CH Alkene), 127.9 (CH Ar), 128.2 (2 CH Ar), 129.4 (CH alkene), 131.6 (2 CH Ar), 170.8 (C ester).

2-(phenylethynyl)but-3-en-1-yl acetate (Minor Product)

$^1$H NMR ($CDCl_3$, 500 MHz) δ 2.09 (s, 3H, $CH_3$), 3.21 (dt, J=7.0 and 6.0 Hz, 1H, CH), 4.18 (dd, J=10.6 and 7.0 Hz, 1H, $CH_2$), 4.24 (dd, J=10.6 and 7.0 Hz, 1H, $CH_2$), 5.26 (dt, J=10.0 and 1.3 Hz, 1H, $CH_2$ alkene), 5.48 (dt, J=17.0 and 1.3 Hz, 1H, $CH_2$ alkene), 5.86 (ddd, J=17.0, 10.0 and 6.0 Hz, 1H, CH alkene), 7.27-7.32 (m, 3H, 3 CH Ar), 7.39-7.45 (m, 2H, 2 CH Ar).
$^{13}$C NMR ($CDCl_3$, 125 MHz), δ 20.9 ($CH_3$), 36.1 (CH), 66.0 ($CH_2$), 84.6 (C alkyne), 86.4 (C alkyne), 117.8 ($CH_2$ Alkene), 123.1 (C Ar), 128.1 (CH Ar), 128.3 (2 CH Ar), 131.7 (2 CH Ar), 133.6 (CH alkene), 170.8 (C ester).

Example 6

Preparation of Ethyl (E)-9-acetoxynon-7-en-4-ynoate 0.66 g (0.25eq) of triethylamine was introduced into a stirred suspension of 0.31 g (0.05 eq) of nickel dichloride hexahydrate and 0.68 g (0.125 eq) of triisopropylphosphite in 3.6 ml of isopropylacetate. 4.48 g (1eq) of 1,4-Diacetoxy (Z)-But-2-ene then 3.28 g (1eq) of ethyl 4-pentynoate were introduced and the mixture was stirred at 20° C. overnight.

Then the reaction was treated by aqueous Na$_2$EDTA followed by diluted potassium carbonate. The reaction mixture containing 30% GC of unreacted ethyl 4-pentynoate, 45% GC of ethyl 9-acetoxynon-7-en-4-ynoate and 17% GC of ethyl 6-(acetoxymethyl)oct-7-en-4-ynoate (72/28 linear/branched ratio) was purified by chromatography on silica gel (30/50 petroleum ether/Et2O 10/0 to 8/2) for pure products isolation Ethyl 9-acetoxynon-7-en-4-ynoate (Major Product)

$^1$H NMR (CDCl$_3$, 500 MHz) δ 1.26 (t, J=7.1 Hz, 3H, CH$_3$), 2.07 (s, 3H, CH$_3$), 2.51 (s, 4H, 2 CH$_2$), 2.93 (d, J=5.0 Hz, 2H, CH$_2$), 4.16 (q, J=7.1 Hz, 2H, CH$_2$), 4.55 (d, J=6.0 Hz, 2H, CH$_2$), 5.74 (dt, J=15.2 and 5.0 Hz, 1H, CH alkene), 5.84 (dt, J=15.2 and 6.0 Hz, 1H, CH alkene).
$^{13}$C NMR (CD$_2$Cl$_2$, 125 MHz), δ 14.4 (CH$_3$), 15.1 (CH$_2$), 21.1 (CH$_3$), 22.0 (CH$_2$), 34.3 (CH$_2$), 60.9 (CH$_2$), 64.7 (CH$_2$), 77.3 (C alkyne), 81.4 (C alkyne), 125.8 (CH Alkene), 130.2 (CH alkene), 170.9 (C ester), 172.3 (C ester).
(Note: $^{13}$C NMR spectrum given in CD$_2$Cl$_2$ instead of CDCl$_3$ due to some signal of quaternary carbon of alkyne moiety hidden in CDCl$_3$).

Ethyl 6-(acetoxymethyl)oct-7-en-4-ynoate (Minor Product)

$^1$H NMR (CDCl$_3$, 500 MHz) δ 1.26 (t, J=7.1 Hz, 3H, CH$_3$), 2.07 (s, 3H, CH$_3$), 2.52 (s, 4H, 2 CH$_2$), 3.37 (dt, J=7.1 and 6.0 Hz, 1H, CH), 4.03 (dd, J=10.5 and 7.1 Hz, 1H, CH$_2$), 4.10 (dd, J=10.5 and 7.1 Hz, 1H, CH$_2$), 4.15 (q, J=7.1 Hz, 2H, CH$_2$), 5.18 (dt, J=10.1 and 1.3 Hz, 1H, CH$_2$ alkene), 5.37 (dt, J=16.5 and 1.3 Hz, 1H, CH$_2$ alkene), 5.75 (ddd, J=16.5, 10.1 and 6.0 Hz, 1H, CH alkene).
$^{13}$C NMR (CDCl$_3$, 125 MHz), δ 14.2 (CH$_3$), 14.8 (CH$_2$), 20.9 (CH$_3$), 33.9 (CH$_2$), 35.4 (CH), 60.6 (CH$_2$), 66.2 (CH$_2$), 77.7 (C alkyne), 82.9 (C alkyne), 113.4 (CH$_2$ Alkene), 134.1 (CH alkene), 170.8 (C ester), 172.0 (C ester).

Example 7

Preparation of (2E,7E)-9-hydroxy-7-methylnona-2,7-dien-5-vn-1-yl acetate 0.66 g (0.25eq) of triethylamine was introduced into a stirred suspension of 0.32 g (0.05 eq) of nickel diacetate tetrahydrate and 0.68 g (0.125 eq) of triisopropylphosphite in 3.6 ml of isopropylacetate. 4.48 g (1eq) of 1,4-Diacetoxy (Z)-But-2-ene then 2.50 g (1eq) of (E)-3-methylpent-2-en-4-yn-1-ol were introduced and the mixture was stirred at 20° C. for 4 h. Then the reaction was treated by aqueous Na$_2$EDTA followed by diluted potassium carbonate. The reaction mixture containing 17% GC of unreacted (E)-3-methylpent-2-en-4-yn-1-ol, 54% GC of (2E,7E)-9-hydroxy-7-methylnona-2,7-dien-5-yn-1-yl acetate and 21% GC of (E)-7-hydroxy-5-methyl-2-vinylhept-5-en-3-yn-1-yl acetate (72/28 linear/branched ratio) was purified by chromatography on silica gel (30/50 petroleum ether/Et2O 10/0 to 6/4) for pure products isolation.

(2E,7E)-9-hydroxy-7-methylnona-2,7-dien-5-yn-1-yl acetate (Major Product)

$^1$H NMR (CDCl$_3$, 500 MHz) δ 1.82 (broad s, 3H, CH$_3$), 1.86 (broad s, 1H, OH), 2.07 (s, 3H, CH$_3$), 3.09 (broad d, J=4.8 HZ, 2H, CH$_2$), 4.21 (d, J=7.0 Hz, 2H, CH$_2$), 4.56 (dd, J=6.2 and 1.1 Hz, 2H, CH$_2$), 5.77 (broad dt, J=15.4 and 4.8 Hz, 1H, CH alkene), 5.86 (dtt, J=15.4, 6.2 and 1.4, 1H, CH alkene), 5.95 (broad tq, J=7.0 and 1.3 Hz, 1H, CH alkene).
$^{13}$C NMR (CDCl$_3$, 125 MHz), δ 17.8 (CH$_3$), 21.0 (CH$_3$), 22.3 (CH$_2$), 59.0 (CH$_2$), 64.5 (CH$_2$), 84.3 (C alkyne), 85.2 (C alkyne), 120.8 (C alkene), 125.6 (CH alkene), 129.5 (CH alkene), 134.8 (CH alkene), 170.9 (C ester).

(E)-7-hydroxy-5-methyl-2-vinylhept-5-en-3-yn-1-yl acetate (Minor Product)

$^1$H NMR (CDCl$_3$, 500 MHz) δ 1.75 (broad s, 1H, OH), 1.83 (broad s, 3H, CH$_3$), 2.08 (s, 3H, CH$_3$), 3.52 (q, J=6.6 Hz, 1H, CH), 4.10 (dd, J=10.6 and 6.6 Hz, 1H, CH$_2$), 4.15 (dd, J=10.6 and 6.6 Hz, 1H, CH$_2$), 4.22 (d, J=6.8 Hz, 2H, CH$_2$), 5.22 (dt, J=10.0 and 1.3 Hz, 1H, CH$_2$ alkene), 5.40 (dt, J=17.0 and 1.3 Hz, 1H, CH$_2$ alkene), 5.79 (ddd, J=17.0, 10.0 and 6.6 Hz, 1H, CH alkene), 5.97 (tq, J=6.8 and 1.4 Hz, 1H, CH alkene)
$^{13}$C NMR (CDCl$_3$, 125 MHz), δ 17.7 (CH$_3$), 20.9 (CH$_3$), 59.0 (CH$_2$), 66.0 (CH$_2$), 84.6 (C alkyne), 86.8 (C alkyne), 117.7 (CH$_2$ alkene), 120.6 (C alkene), 133.7 (CH alkene), 135.2 (CH alkene), 170.9 (C ester).

Example 8

Preparation of (E)-8-hydroxyoct-2-en-5-yn-1-yl acetate 0.66 g (0.25eq) of triethylamine was introduced into a stirred suspension of 0.32 g (0.05 eq) of nickel diacetate tetrahydrate and 0.68 g (0.125 eq) of triisopropylphosphite in 3.6 ml of isopropylacetate. 4.48 g (1eq) of 1,4-Diacetoxy (Z)-But-2-ene then 1.82 g (1eq) of 3-Butyn-1-ol were introduced and the mixture was stirred at 20° C. for 24 h. Then the reaction was treated by aqueous Na$_2$EDTA followed by diluted potassium carbonate. Thanks to both GC-MS and NMR analysis, crude mixture was determined to contain 51% GC of unreacted 3-Butyn-1-ol, 32% GC of (E)-8-hydroxyoct-2-en-5-yn-1-yl acetate and 11% GC of 6-hydroxy-2-vinylhex-3-yn-1-yl acetate (75/25 linear/branched ratio).

Example 9

Preparation of (E)-undec-2-en-5-yn-1-yl benzoate 0.66 g (0.25eq) of triethylamine was introduced into a stirred suspension of 0.31 g (0.05 eq) of nickel dichloride hexahydrate and 0.68 g (0.125 eq) of triisopropylphosphite in 3.6 ml of isopropylacetate. 7.70 g (1eq) of (Z)-but-2-ene-1,4-diyl dibenzoate then 2.5 g (1eq) of heptyne were introduced and the mixture was stirred at 20° C. for 20 h. Then the reaction was treated by aqueous Na$_2$EDTA followed by diluted potassium carbonate. Thanks to both GC-MS and NMR analysis, crude mixture was determined to contain 51% GC of unreacted heptyne, 26% GC of (E)-undec-2-en-5-yn-1-yl benzoate and 10% GC of 2-vinylnon-3-yn-1-yl benzoate (72/28 linear/branched ratio).

Example 10

Preparation of Dec-1-en-4-yne 0.66 g (0.25eq) of triethylamine was introduced into a stirred suspension of 0.32 g (0.05 eq) of nickel diacetate tetrahydrate and 0.68 g (0.125 eq) of triisopropylphosphite in 3.6 ml of isopropylacetate. 2.60 g (1eq) of allyl acetate then 2.5 g (1eq) of heptyne were introduced and the mixture was stirred at 20° C. for 18 h. Then the reaction was treated by aqueous Na$_2$EDTA followed by diluted potassium carbonate. Thanks to both GC-MS and NMR analysis, crude mixture was determined to contain 10% GC of unreacted heptyne and 78% GC of dec-1-en-4-yne.

Example 11

Preparation of (E)-undec-2-en-5-yne 0.66 g (0.25eq) of triethylamine was introduced into a stirred suspension of 0.32 g (0.05 eq) of nickel diacetate tetrahydrate and 0.68 g (0.125 eq) of triisopropylphosphite in 3.6 ml of isopropylacetate. 2.97 g (1eq) of 3-buten-2-yl acetate then 2.5 g (1eq) of heptyne were introduced and the mixture was stirred at 20° C. for 18 h. Then the reaction was treated by aqueous Na$_2$EDTA followed by diluted potassium carbonate. Thanks to both GC-MS and NMR analysis, crude mixture was determined to contain 10% GC of unreacted heptyne. 40% GC of (E)-undec-2-en-5-yne and 40% GC of 3-methyldec-1-en-4-yne (50/50 linear/branched ratio).

Example 12

Preparation of Ethyl (E)-9-acetoxynon-7-en-4-ynoate 0.66 g (0.25eq) of triethylamine was introduced into a stirred suspension of 0.32 g (0.05 eq) of nickel diacetate tetrahydrate and 0.68 g (0.125 eq) of triisopropylphosphite in 3.6 ml of isopropylacetate. 2.60 g (1eq) of allyl acetate then 3.28 g (1eq) of ethyl 4-pentynoate were introduced and the mixture was stirred at 20° C. for 8 h. Then the reaction was treated by aqueous Na$_2$EDTA followed by diluted potassium carbonate. Thanks to both GC-MS and NMR analysis, crude mixture was determined to contain 13% GC of unreacted ethyl 4-pentynoate and 80% GC of ethyl oct-7-en-4-ynoate.

The invention claimed is:

1. A process for the preparation of a compound of formula (I)

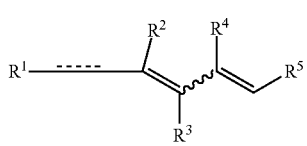

in a form of any one of its stereoisomers or a mixture thereof and wherein the dotted line is a carbon-carbon double or a carbon-carbon triple bond and R$^1$ represents a C$_{1-10}$ hydrocarbon group, optionally comprising one or more hydroxy, C$_{1-15}$ alkoxy, C$_{2-15}$ alkenyloxy, C$_{3-15}$ heterocycloalkyl, C$_{6-10}$ aryloxy and/or C$_{1-4}$ carboxylic ester groups and R$^2$, R$^3$, R$^4$ and R$^5$, independently from each other, represent a hydrogen atom, a C$_{1-3}$ alkyl group or a phenyl group;

comprising the reaction of a compound of formula (II)

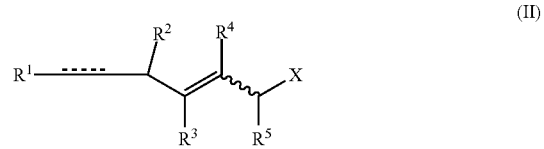

in a form of any one of its stereoisomers and wherein the dotted line, R$^1$, R$^2$, R$^3$, R$^4$ and R$^5$ have the same meaning as defined in formula (I) and X represents a OR$^6$ group, a OC(=O)R$^6$ group, a OC(=O)OR$^6$ group or a OSO$_2$R$_6$ group, wherein R$^6$ is a hydrogen atom or a C$_{1-4}$ alkyl group or a phenyl group;
with a nickel catalyst.

2. The process according to claim 1, wherein R$^1$ represents a linear C$_{1-10}$ alkyl group, a linear C$_{2-10}$ alkenyl group, a branched C$_{3-10}$ alkyl or alkenyl group, or a C$_{6-10}$ aryl group, optionally comprising one hydroxy or C$_{1-4}$ carboxylic ester group.

3. The process according to claim 1, wherein R$^1$ represents a linear C$_{4-8}$ alkyl group.

4. The process according to according to claim 1, wherein X represents a OC(=O)R$^6$ group wherein R$^6$ is a C$_{1-3}$ alkyl group.

5. The process according to claim 1, wherein X represents an acetate group.

6. The process according to claim 1, wherein each of R$^2$, R$^3$, R$^4$ and R$^5$ are a hydrogen atom.

7. The process according to claim 1, wherein the nickel catalyst is of formula

 (III) or

 (III') ... or

 (III'') or

 (III''')

wherein each P represents, independently from each other, a C$_3$-C$_{30}$ monodentate ligand wherein the coordinating groups are one phosphorus atom and each PP represents, independently from each other, a C$_5$-C$_{50}$ bidentate ligand wherein the coordinating groups are two phosphorus atoms; and M and L, independently from each other, are an anionic or neutral ligand, provided that when M is a neutral ligand, L is a neutral ligand and when M is an anionic ligand, L is an anionic ligand.

8. The process according to claim 7, wherein P is a monophosphite of formula P(OR$^7$)$_3$ wherein R$^7$ is C$_{1-6}$ linear alkyl group, a C$_{3-6}$ branched alkyl group or a phenyl group.

9. The process according to claim 7, wherein the nickel catalyst of formula (III), (III') (III'') or (III''') is formed in situ by the reaction between a nickel(II) complex and a phosphite or phosphine in the presence of a base.

10. The process according to claim 1, wherein the compound of formula (I) is of formula

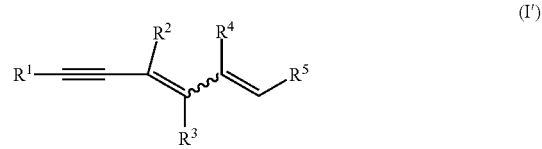

in a form of any one of its stereoisomers or a mixture thereof and wherein $R^1$ represents a $C_{1-10}$ hydrocarbon group, optionally comprising one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups and $R^2$, $R^3$, $R^4$ and $R^5$, independently from each other, represent a hydrogen atom, a $C_{1-3}$ alkyl group or a phenyl group; and the compound of formula (II) is of formula

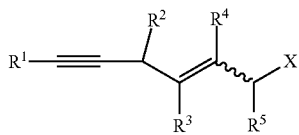

(II')

in a form of any one of its stereoisomers and wherein $R^1$, $R^2$, $R^3$, $R^4$, $R^5$ and X have the same meaning as defined in formula (I').

11. The process according to claim 1, wherein the compound of formula (I) is of formula

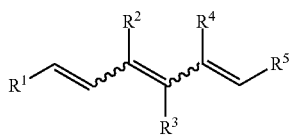

(I'')

in a form of any one of its stereoisomers or a mixture thereof and wherein $R^1$ represents a $C_{1-10}$ hydrocarbon group, optionally comprising one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups and $R^2$, $R^3$, $R^4$ and $R^5$, independently from each other, represent a hydrogen atom, a $C_{1-3}$ alkyl group or a phenyl group; and the compound of formula (II) is of formula

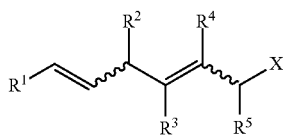

(II'')

in a form of any one of its stereoisomers and wherein $R^1$, $R^2$, $R^3$, $R^4$, $R^5$ and X have the same meaning as defined in formula (I').

12. The process according to claim 11, wherein the compound of formula (II'') is obtained by the reduction of the compound of formula (II').

13. A process for the preparation of a compound of formula (IV)

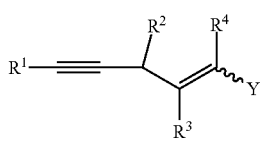

(IV)

in a form of any one of its stereoisomers and wherein $R^1$ represents a $C_{1-10}$ hydrocarbon group, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$ and $R^4$, independently from each other, represent a hydrogen atom, a $C_{1-3}$ alkyl group or a phenyl group and Y is a hydrogen atom, a $C_{1-3}$ alkyl group, or a $CHR^5X$ group wherein $R^5$ is a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group;

by reacting together a compound of formula

(V)

in a form of any one of its stereoisomers and wherein $R^1$ has the same meaning as defined in formula (IV);

with a compound of formula

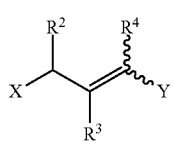

(VI)

in a form of any one of its stereoisomers and wherein X, Y, $R^2$, $R^3$ and $R^4$ have the same meaning as defined in formula (IV);

in the presence of a nickel catalyst.

14. The process according to claim 13, wherein the nickel catalyst is of formula

 [Ni(P)$_4$]    (III) or

 [Ni(PP)$_2$]    (III') ... or

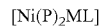 [Ni(P)$_2$ML]    (III'') or

 [Ni(PP)ML]    (III''')

wherein each P represents, independently from each other, a $C_3$-$C_{30}$ monodentate ligand wherein the coordinating groups are one phosphorus atom and each PP represents, independently from each other, a $C_5$-$C_{50}$ bidentate ligand wherein the coordinating groups are two phosphorus atoms; and M and L, independently from each other, are an anionic or neutral ligand, provided that when M is a neutral ligand, L is a neutral ligand and when M is an anionic ligand, L is an anionic ligand.

15. A compound of formula

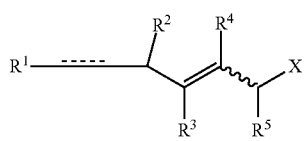

(II)

in a form of any one of its stereoisomers and wherein the dotted line is a carbon-carbon double or a carbon-carbon triple bond; $R^1$ represents a linear or branched $C_{1-10}$ alkyl group, optionally substituted by one or more hydroxy, $C_{1-15}$ alkoxy, $C_{2-15}$ alkenyloxy, $C_{3-15}$ heterocycloalkyl, $C_{6-10}$ aryloxy and/or $C_{1-4}$ carboxylic ester groups; $R^2$, $R^3$, $R^4$ and $R^5$, independently from each other, represent a hydrogen atom, a $C_{1-3}$ alkyl group or a phenyl group and X represents a $OR^6$ group, a $OC(=O)R^6$ group, a $OC(=O)OR^6$ group or a $OSO_2R^6$ group, wherein $R^6$ is a hydrogen atom or a $C_{1-4}$ alkyl group or a phenyl group.

16. The process according to claim 1, wherein $R^1$ represents a pentyl group.

17. The process according to claim 1, wherein
X represents an acetate group;
$R^1$ represents a pentyl group; and
each of $R^2$, $R^3$, $R^4$ and $R^5$ are a hydrogen atom.

18. The process according to claim 15, wherein the nickel catalyst is of formula

[Ni(P)$_4$]  (III) or

[Ni(PP)$_2$]  (III') ... or

[Ni(P)$_2$ML]  (III'') or

[Ni(PP)ML]  (III''')

wherein each P represents, independently from each other, a $C_3$-$C_{30}$ monodentate ligand wherein the coordinating groups are one phosphorus atom and each PP represents, independently from each other, a $C_5$-$C_{50}$ bidentate ligand wherein the coordinating groups are two phosphorus atoms; and M and L, independently from each other, are an anionic or neutral ligand, provided that when M is a neutral ligand, L is a neutral ligand and when M is an anionic ligand, L is an anionic ligand.

19. The process according to claim 16, wherein P is a monophosphite of formula $P(OR^7)_3$ wherein $R^7$ is $C_{1-6}$ linear alkyl group, a $C_{3-6}$ branched alkyl group or a phenyl group.

* * * * *